United States Patent

Bates et al.

[11] Patent Number: 5,129,890
[45] Date of Patent: Jul. 14, 1992

[54] HYDROPHILICALLY COATED FLEXIBLE WIRE GUIDE

[75] Inventors: Brian L. Bates; Thomas A. Osborne, both of Bloomington, Ind.

[73] Assignee: Cook Incorporated, Bloomington, Ind.

[21] Appl. No.: 648,923

[22] Filed: Feb. 1, 1991

Related U.S. Application Data

[63] Continuation of Ser. No. 373,799, Jun. 29, 1989, abandoned.

[51] Int. Cl.[5] ............................................. A61M 25/00
[52] U.S. Cl. .................................... 604/281; 128/657; 128/772; 604/170
[58] Field of Search ............... 128/657, 772, 656, 658; 604/281, 282, 280, 265, 164, 170

[56] References Cited

U.S. PATENT DOCUMENTS

| | | | |
|---|---|---|---|
| 4,884,579 | 12/1989 | Engelson | 128/772 |
| 4,925,445 | 5/1990 | Sakamoto et al. | 604/95 |
| 4,966,163 | 10/1990 | Kraus et al. | 128/772 |
| 4,977,901 | 12/1990 | Ofstead | 128/772 |
| 4,991,602 | 2/1991 | Amplatz et al. | 128/772 |

FOREIGN PATENT DOCUMENTS 9013329  11/1990  World Int. Prop. O. .......... 604/281

Primary Examiner—C. Fred Rosenbaum
Assistant Examiner—C. Maglione
Attorney, Agent, or Firm—Woodard, Emhardtm, Naughton Moriarty & McNett

[57] ABSTRACT

A wire guide comprising an elongate central core and a coil formed of radiopaque material which is positioned substantially concentrically with the elongate central core. The wire guide also comprises a polymer sleeve which encloses the elongated central core. The guide wire further comprises a hydrophilic coating which substantially encloses the polymer sleeve.

16 Claims, 2 Drawing Sheets

HYDROPHILICALLY COATED FLEXIBLE WIRE GUIDE

This application is a continuation of application Ser. No. 373,799, field Jun. 29, 1989, now abandoned.

BACKGROUND OF THE INVENTION

This invention relates to wire guides which may be used for placement of catheters.

One application for which such wire guides are used is the percutaneous placement of a catheter into the vascular system. The procedure involves penetrating an organ, such as a vein or the like, with a needle. The wire guide is then passed through the needle into the organ. The needle is then withdrawn over the wire guide, leaving the wire guide in place in the organ. A catheter is then slid over the wire guide into the organ and further guided by the wire guide through the organ. Such a wire guide can be used, for example, to position a catheter at difficult to reach locations in or around the heart or the like.

Wire guides have heretofore been provided to facilitate the insertion of a catheter into an organ, such as a vein, and further to facilitate the guidance of a catheter through an organ to various locations in a body. Certain prior art wire guides have a coil spring throughout its entire length of the guide and therefore are susceptible to breakage. In addition, use of some prior art wire guides create friction between the coils of the spring and the inner surface of the organ.

In order to overcome such problems, wire guides were developed having a plastic outside surface. Other wire guides have been developed including a hydrophilic coating on the outside surface in order to reduce friction between the outer surface of the wire guide and the inner surface of the organ and further to reduce the likelihood of breakage of the wire guide while in the organ. As regards prior art wire guides having a hydrophilic coating on their outside surface, such coating extends over the entire proximal portion of the wire guide making it difficult for the operator to grip and control the wire guide.

SUMMARY OF THE INVENTION

One embodiment of the present invention might involve a wire guide which includes a elongated central core having a proximal and distal portion. There is provided a coil positioned substantially concentrically with the elongated central core and secured to the distal portion of the elongated central core. The coil includes a proximal and distal portion. There is further provided a polymer sleeve which encloses the proximal portion of the elongated central core. Moreover, a hydrophilic coating encloses the polymer sleeve. In another embodiment of the present invention the proximal portion of hydrophilic coating is positioned so as not to cover the extreme proximal portion of polymer sleeve.

One object of the invention is to provide an improved wire guide.

Another object of the invention is to provide a wire guide in which friction is reduced between the outer surface of the wire guide and the inner surface of the organ.

A further object of the invention is to provide a wire guide having a good base for a hydrophilic coating.

Still another object of the invention is to provide a wire guide which has an improved appearance and surface finish.

Another object of the invention is to provide a wire guide which is easier for the operator to grip and consequently easier for the operator to control.

DESCRIPTION OF THE PREFERRED EMBODIMENT

Figure 1:
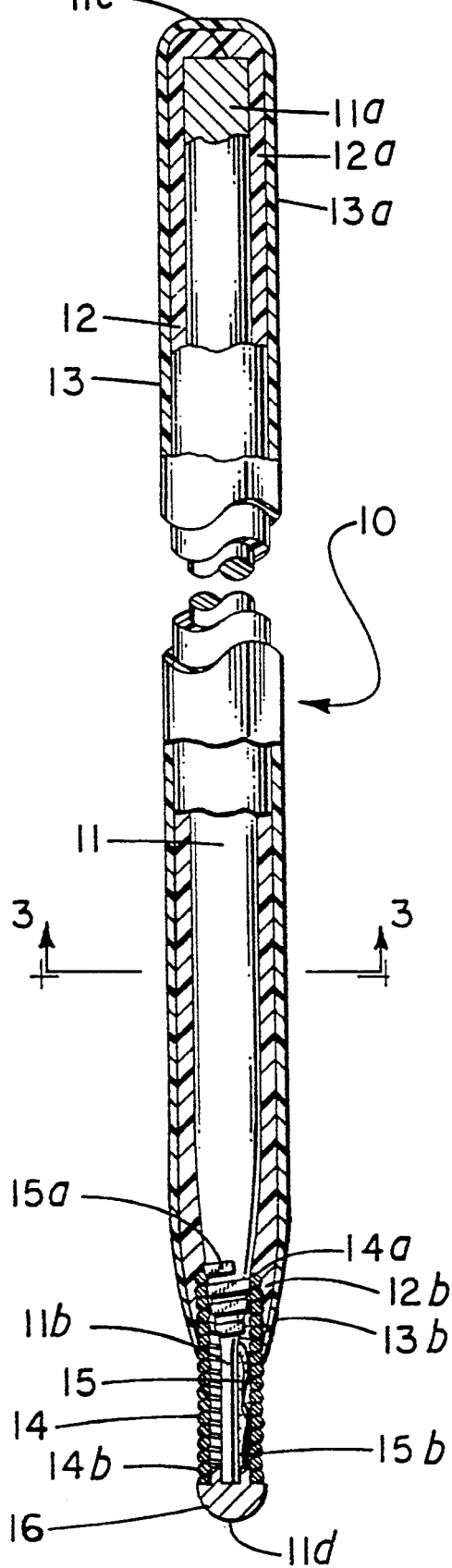
FIG. 1 is a side elevational view partially in cross section of a wire guide incorporating the present invention.

For the purposes of promoting an understanding of the principles of the invention, reference will now be made to the embodiment illustrated in the drawings and specific language will be used to describe the same. It will nevertheless be understood that no limitation of the scope of the invention is thereby intended, such alterations and further modifications in the illustrated device, and such further applications of the principles of the invention as illustrated therein being contemplated as would normally occur to one skilled in the art to which the invention relates.

Figure 2:
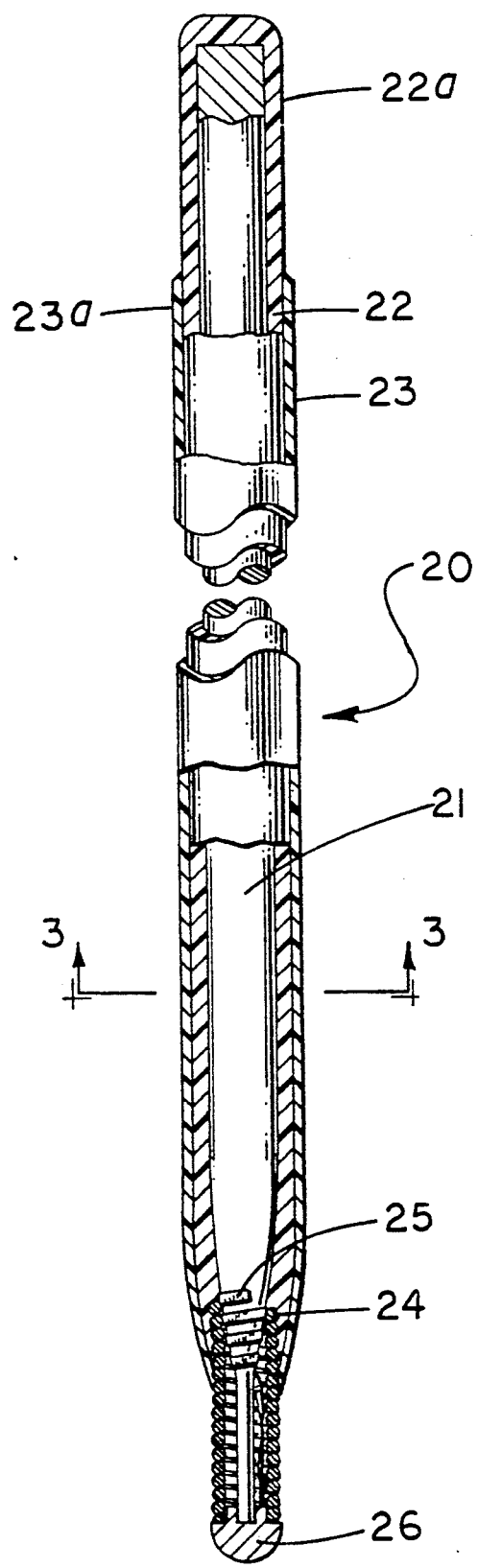
FIG. 2 is a side elevational view partially in cross section of an alternative embodiment of the invention.

Referring now to FIGS. 1 and 2, there is illustrated a wire guide 10 which may have a diameter ranging from 0.012 to 0.065 inches and a length ranging from 20.0 to 460.0 centimeters. Wire guide 10 includes a flexible elongated central core 11 having a uniform thickness at its proximal portion 11a and tapered at its distal portion 11b. The length of the taper at distal portion of elongate central core 11b can vary from 1.0 to 30.0 centimeters, however, such taper length is typically 10.0 to 15.0 centimeters. The elongated central core 11 also includes a proximal end 11c and a distal end 11d. The central core 11 may be formed of any suitable shape memory metal, however, it is preferred to construct elongate central core 11 from a nickel titanium alloy such as Nitinol. When Nitinol or other shape memory material is used, the diameter of the elongate central core 11 should be very near the diameter of wire guide 10 owing to its shape memory or superelastic properties. Nitinol does not have as great a stiffness or tensile strength as other non shape memory materials such as stainless steel. Therefore, in order to overcome the resulting loss in stiffness, a much larger diameter Nitinol elongate central core is used.

The distal portion 11b of elongate central core is affixed to an elongate coil 14 at either its proximal portion 14a or its distal portion 14b or both. Such affixation may be achieved by welding, soldering or glue bonding. Elongate coil 14 may be made of platinum in order to give wire guide 10 extremely good radiopacity (better than stainless steel) and a soft, floppy distal portion. The coil 14 may range in length from 1.0 to 15.0 centimeters, however, its length is typically 2.0 to 3.0 centimeters.

Also affixed to distal portion of elongate central core 11b is a safety ribbon wire 15. The safety ribbon wire 15 may be made of a suitable material such as stainless steel. Safety ribbon wire 15 has a proximal portion 15a and a distal portion 15b. The safety ribbon wire 15 may be affixed to elongate central core 11 by welding, soldering or glue bonding the above two members together. One possibility is to affix the distal portion of elongate member 11b to the proximal portion of safety ribbon wire 15a.

A thin polymer sleeve 12 completely encloses proximal portion of elongate central core 11a and proximal end of elongate central core 11c. The resulting outer diameter of polymer sleeve 12 positioned on top of elongate central core 11 is substantially the same as the diameter of wire guide 10. Polymer sleeve 12 has a proximal portion 12a and a distal portion 12b. Distal portion of polymer sleeve 12b partially encloses distal portion of elongate central core 11b. In addition, distal portion of polymer sleeve 12b partially covers the proximal portion 14a of the coil and the proximal portion 15a of safety ribbon wire. Polymer sleeve 12 can be formed from any suitable material with appropriate bonding and frictional properties described in this specification. In the preferred embodiment, polymer sleeve 12 is made of polyurethane.

The polymer sleeve 12 creates a good base for a hydrophilic coating 13 and gives wire guide 10 a good appearance and surface finish. The hydrophilic coating 13 includes a proximal portion 13a and a distal portion 13b. Proximal portion of hydrophilic coating 13a encloses proximal portion of polymer sleeve 12a, proximal portion of elongate central core 11a and proximal end of elongate central core 11c. The distal portion of hydrophilic coating 13b encloses distal portion of polymer sleeve 12b and partially encloses distal portion of elongate central core 11b. In addition, distal portion of hydrophilic coating 13b partially covers the proximal portion of the coil 14a and proximal portion of safety ribbon wire 15a. The hydrophilic coating 13 makes wire guide 10 extremely slick and allows it to be easily maneuvered through tortuous areas.

A rounded metallic protrusion 16 is disposed on the distal extremity of wire guide 10. The metallic protrusion 16 can be affixed to distal portion of safety ribbon wire 15b. Such protrusion is formed by a weld or solder.

Figure 3:
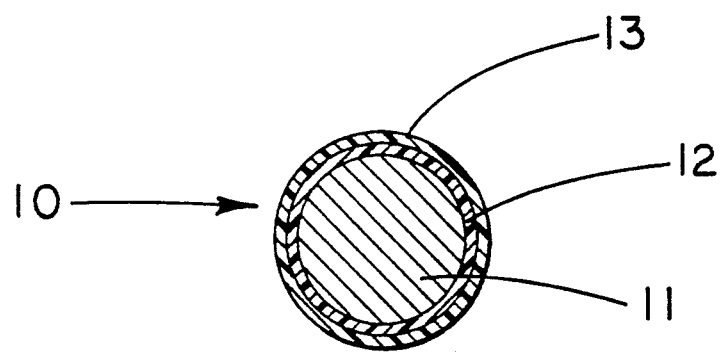
FIG. 3 is a cross-sectional view taken along the line 3—3 of both FIGS. 1 and 2.

Another embodiment of a wire guide incorporating the present invention is shown in FIG. 3 in which the wire guide 20 includes an elongated central core 21, a polymer sleeve 22, a hydrophilic coating 23, an elongated coil 24, a safety ribbon wire 25 and a rounded metallic protrusion 26. The alternate embodiment of the wire guide shown in FIG. 2 is identical to the embodiment of the wire guide shown in FIG. 1 in all respects except that in the embodiment shown in FIG. 2, the proximal portion of hydrophilic coating 23a proximally terminates so as not to cover the extreme proximal portion of polymer sleeve 22a. The non-hydrophilically coated proximal portion of polymer sleeve 22a may vary in length from 10.0 to 30.0 centimeters. The benefit of not coating the extreme proximal portion of wire guide 20 with the hydrophilic material is to facilitate better gripping and consequently greater control of wire guide 20 during its use.

While the invention has been illustrated and described in detail in the drawings and foregoing description, the same is to be considered as illustrative and not restrictive in character, it being understood that only the preferred embodiment has been shown and described and that all changes and modifications that come within the spirit of the invention are desired to be protected.

What is claimed is:

1. A wire guide comprising:

a mandrel of shape memory material, said mandrel having a distal end and a proximal end;

a distal end portion of radiopaque material having a distal end and a proximal end, said distal end portion of radiopaque material being secured to the distal portion of said mandrel of shape memory material;

a first thin coating of polymeric material applied along the length of said mandrel from the proximal end of said mandrel to the proximal end of said distal end portion of radiopaque material;

a second thin coating of hydrophilic material applied along the length of said first coating from the proximal end of said distal end portion of radiopaque material to a point short of the proximal end of said mandrel and terminating thereat, whereby said first thin coating of polymeric material is exposed near the proximal end of said wire guide; and wherein said first thin coating of polymeric material has a substantially higher coefficient of friction than said second thin coating of hydrophilic material, and wherein said first thin coating of polymeric material forms a bonding base between said shape memory material and said hydrophilic material along the length of said hydrophilic material and further facilitates gripping and handling of said wire guide near the proximal end of said wire guide.

2. The wire guide of claim 1 wherein said polymeric material is polyurethane.

3. The wire guide of claim 2 wherein said shape memory material is a nickel titanium alloy.

4. The wire guide of claim 3 in which said mandrel is substantially uniform in diameter along its length from the proximal end of said mandrel to the area of attachment between said mandrel and the distal end portion of radiopaque material.

5. The wire guide of claim 1 wherein said shape memory material is a nickel titanium alloy.

6. The wire guide of claim 5 wherein said radiopaque material is platinum.

7. The wire guide of claim 1 wherein said radiopaque material is platinum.

8. The wire guide of claim 1 in which said mandrel is substantially uniform in diameter along its length from the proximal end of said mandrel to the area of attachment between said mandrel and said distal end portion of radiopaque material.

9. A wire guide comprising:

a mandrel of shape memory material, said mandrel having a distal end and a proximal end;

a coil of radiopaque material having a distal end and a proximal end, said coil being secured to the distal portion of said mandrel of shape memory material and being positioned substantially concentrically thereabout;

a first thin coating of polymeric material applied along the length of said mandrel from the proximal end of said mandrel to the proximal end of said coil;

a second thin coating of hydrophilic material applied along the length of said first coating from the proximal end of said coil to a point short of the proximal end of said mandrel and terminating thereat, whereby said first thin coating of polymeric material is exposed near the proximal end of said wire guide; and wherein said first thin coating of polymeric material has a substantially higher coefficient of friction than said second thin coating of hydrophilic material, and wherein said first thin coating of polymeric material forms a bonding base between said shape memory material and said hydrophilic material along the length of said hydrophilic material and further facilitates gripping and handling of said wire guide near the proximal end of said wire guide.

10. The wire guide of claim 9 wherein said polymeric material is polyurethane.

11. The wire guide of claim 10 wherein said shape memory material is a nickel titanium alloy.

12. The wire guide of claim 11 in which said mandrel is substantially uniform in diameter along its length from the proximal end of said mandrel to the area of attachment between said mandrel and said coil.

13. The wire guide of claim 9 wherein said shape memory material is a nickel titanium alloy.

14. The wire guide of claim 13 wherein said radiopaque material is platinum.

15. The wire guide of claim 9 wherein said radiopaque material is platinum.

16. The wire guide of claim 9 in which said mandrel proximal is substantially uniform in diameter along its length from the proximal end of said mandrel to the area of attachment between said mandrel and said coil.

* * * * *

UNITED STATES PATENT AND TRADEMARK OFFICE
CERTIFICATE OF CORRECTION

PATENT NO. : 5,129,890

DATED : July 14, 1992

INVENTOR(S) : Brian L. Bates et al.

It is certified that error appears in the above-identified patent and that said Letters Patent is hereby corrected as shown below:

On the title page, under "Attorney, Agent, or Firm," please change "Emhardtm" to --Emhardt--.

In column 1, line 6, please change "field" to --filed--.

In column 2, line 46, please insert a period after "10".

In column 2, line 47, please change "owing" to --Owing-- and change the period to a comma.

In column 2, line 49, please change "non shape" to --non-shape--.

Signed and Sealed this

Tenth Day of August, 1993

Attest:

MICHAEL K. KIRK

Attesting Officer

Acting Commissioner of Patents and Trademarks